United States Patent [19]

Lee et al.

[11] Patent Number: 5,151,161

[45] Date of Patent: * Sep. 29, 1992

[54] SEPARATION OF OLEFINIC HYDROCARBONS BY EXTRACTIVE DISTILLATION

[75] Inventors: Fu-Ming Lee; Ronald E. Brown, both of, Bartlesville, Okla.

[73] Assignee: Phillips Petroleum Company, Bartlesville, Okla.

[*] Notice: The portion of the term of this patent subsequent to Jul. 16, 2008 has been disclaimed.

[21] Appl. No.: 731,686

[22] Filed: Jul. 17, 1991

[51] Int. Cl.⁵ .............................................. B01D 3/40
[52] U.S. Cl. ........................................ 203/51; 203/58; 585/857; 585/860; 585/865
[58] Field of Search ............. 203/51, 58; 585/833, 585/860, 865, 857

[56] References Cited

U.S. PATENT DOCUMENTS

| | | |
|---|---|---|
| 2,508,723 | 5/1950 | Mayland et al. ................. 260/666 |
| 3,723,256 | 3/1973 | Thompson ............................ 203/43 |
| 3,803,258 | 4/1974 | Weitz et al. ......................... 203/51 |
| 4,053,369 | 10/1977 | Cines ................................... 203/52 |
| 4,141,925 | 2/1979 | Pavlov et al. ....................... 203/51 |
| 4,921,581 | 5/1990 | Lee et al. ............................. 203/56 |
| 4,944,849 | 7/1990 | Lee ....................................... 203/55 |
| 4,948,470 | 8/1990 | Lee ....................................... 203/51 |
| 4,948,472 | 8/1990 | Lee et al. ............................. 203/55 |
| 4,954,224 | 9/1990 | Brown et al. ....................... 203/51 |
| 4,955,468 | 9/1990 | Lee ....................................... 203/53 |
| 5,032,232 | 7/1991 | Lee et al. . |

Primary Examiner—Virginia Manoharan
Attorney, Agent, or Firm—K. K. Brandes

[57] ABSTRACT

The separation of alkadienes from close-boiling alkenes by extractive distillation employes as solvent N-methyl-2-thiopyrrolidone, alone or in admixture with unsubstituted sulfolane (cyclotetramethylene sulfone), or a mixture of unsubstituted sulfone and N-methyl-2-pyrrolidone. The separation of cycloalkadienes from close-boiling alkadienes by extractive distillation employs N-methyl-2-thiopyrrolidone as solvent.

13 Claims, 1 Drawing Sheet

SEPARATION OF OLEFINIC HYDROCARBONS BY EXTRACTIVE DISTILLATION

BACKGROUND OF THE INVENTION

This invention relates to the separation of alkadienes (aliphatic diolefins) from close-boiling alkenes (aliphatic monoolefins) by extractive distillation. In another aspect, this invention relates to the separation of cycloalkadienes (cyclodiolefins) from close-boiling alkadienes (aliphatic diolefins) by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, Jun. 28, 1982, pages 91-95. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

SUMMARY OF THE INVENTION

It is an object of this invention to provide a process for separating alkadienes from close-boiling alkenes by extractive distillation employing a selective solvent (also referred to as extractant or entrainer). It is another object of this invention to provide a process for separating cycloalkadienes from alkadienes by extractive distillation employing a selective solvent. Other objects and advantages will be apparent from the detailed description of the invention and the appended claims.

In accordance with this invention, a process for separating at least one alkadiene containing 4-9 carbon atoms per molecule from at least one close-boiling alkene by extractive distillation of a feed comprising (preferably consisting essentially of) said at least one alkadiene and said at least one alkene employs a solvent consisting essentially of at least one liquid selected from the group consisting of N-methyl-2-thiopyrrolidone, mixtures of cyclotetramethylene sulfone (unsubstituted sulfolane) and N-methyl-2-thiopyrrolidone, and mixtures of cyclotetramethylene sulfone and N-methyl-2-pyrrolidone.

Also, in accordance with this invention, a process for separating at least one cycloalkadiene containing 5-9 carbon atoms per molecule from at least one close-boiling alkadiene by extractive distillation of a feed comprising (preferably consisting essentially of) said at least one alkadiene and said at least one alkene employs a solvent consisting essentially of N-methyl-2-thiopyrrolidone.

DETAILED DESCRIPTION OF THE INVENTION

Figure 1:
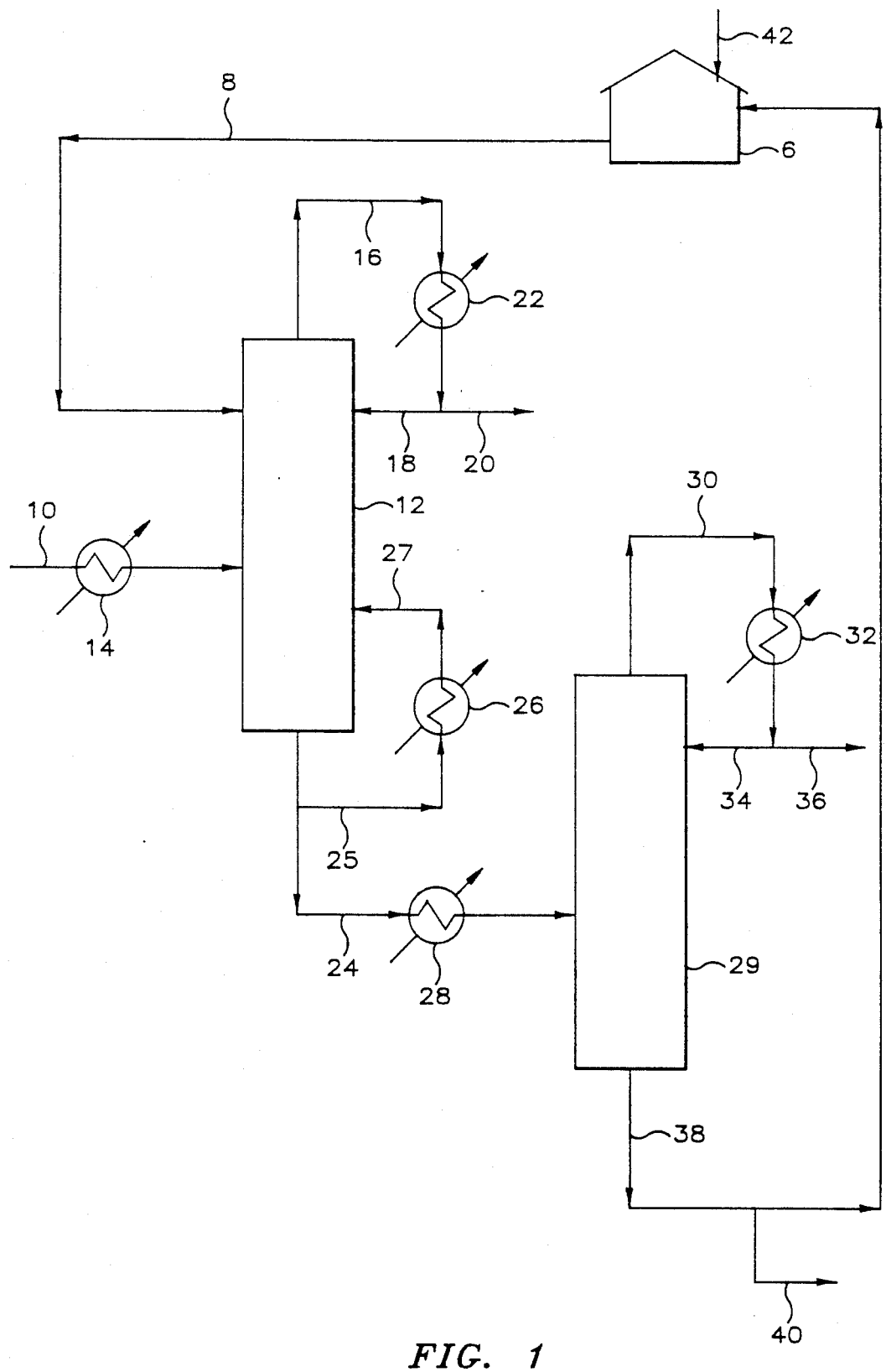
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity. The term "close-boiling" as used herein, means that the feed components have nearly the same boiling point at atmospheric pressure.

In the first embodiment of this invention, any hydrocarbon feed which comprises at least one alkadiene containing 4-9 carbon atoms per molecule and at least one close-boiling alkene (preferably containing 4-10 carbon atoms per molecule) can be used. Preferably, the boiling points (at atmospheric pressure conditions, i.e., at about 1 atm.) of the alkadiene(s) and of the alkene(s) to be separated by extractive distillation process of this invention, are in the range of from about 15° F. to about 400° F., more preferably about 100°-350° F. Generally, the boiling points of the alkadiene(s) and of the alkene(s) differ by about 0.2°-10° F. (preferably about 0.5°-5° F.), at about 1 atm. Preferably, the alkadiene content in the feed is about 5-95 weight-% (more preferably about 20-80 weight-%), and the alkene content is about 5-95 weight-% (more preferably about 20-80 weight-%).

Non-limiting examples of suitable feed alkadienes are 1,2-butadiene, 1,3-butadiene, isoprene, 1,2-pentadiene, 1,3-pentadiene, 2,4-pentadiene, 1,2-hexadiene, 1,3-hexadiene, 1,4-hexadiene, 1,5-hexadiene, 2,4-hexadiene, 2-methyl-1,2-pentadiene, 3-methyl-1,2-pentadiene, 1,2-heptadiene, 1,3-heptadiene, 1,4-heptadiene, 2-methyl-1,2-hexadiene, 3-methyl-1,2-hexadiene, 2-methyl-1,3-hexadiene, 3-methyl-1,3-hexadiene, 1,2-octadiene, 1,3-octadiene, 1,4-octadiene, 1,5-octadiene, 2-methyl-1,2-heptadiene, 3-methyl-1,2-heptadiene, 2-methyl-1,3-heptadiene, 3-methyl-1,3-heptadiene, 3-ethyl-1,2-hexadiene, 2-methyl-3-ethyl-1,3-pentadiene, 1,2-nonadiene, 1,3-nonadiene, 2,4-nonadiene, 2-methyl-1,2-octadiene, 3-methyl-1,2-octadiene, 3-methyl-1,3-octadiene, 3-ethyl-1,3-heptadiene, 3-ethyl-1,4-heptadiene, and mixtures thereof; in particular 1,5-hexadiene or 2-methyl-1,3-pentadiene.

Non-limiting examples of suitable alkenes are 1-butene, 2-butene, 2-methylpropene (isobutene), 1-pentene, 2-pentene, 2-methyl-1-butene, 1-hexene, 2-hexene, 3-hexene, 2-methyl-1-pentene, 2-methyl-2-pentene, 3-methyl-1-pentene, 2,3-dimethyl-1-butene, 1-heptene, 2-heptene, 3-heptene, 2-methyl-1-hexene, 2-methyl-2- hexene, 3-methyl-2-hexene, 3-methyl-3-hexene, 3,3-dimethyl-1-pentene, 1-octene, 2-octene, 3-octene, 2-methyl-1-heptene, 1-nonene, 2-nonene, 3-nonene, 1-decene, 2-decene, and the like, and mixtures thereof; in particular 1-hexene or 2-heptene.

In the second embodiment of this invention, any hydrocarbon feed which contains at least one cycloalkadiene containing 5-9 carbon atoms per molecule and at least one close-boiling alkadiene (preferably containing 4-9 carbon atoms per molecule) can be used. Preferably, the boiling points (at atmospheric pressure conditions) of the cycloalkadiene(s) and of the alkadiene(s) to be separated by the extractive distillation process of this invention, are in the range of about 80° F. to about 400° F., more preferably 100°–550° F. Generally, the boiling points of the cycloalkadiene(s) and of the alkadiene(s) differ by about 0.2°–10° F. (preferably about 0.5°–5° F.), at about 1 atm. Preferably, the cycloalkadiene content in the feed is about 5-95 weight-% (more preferably about 20-80 weight-%), and the alkadiene content in the feed is about 5-95 weight-% (preferably about 20-80 weight-%).

Non-limiting examples of suitable alkadienes are listed above. Non-limiting examples of suitable cycloalkadienes are 1,2-cyclopentadiene, 1,3-cyclopentadiene, 1,2-cyclohexadiene, 1,3-cyclohexadiene, 1-methyl-1,2-cyclopentadiene, 2-methyl-1,2-cyclopentadiene, 3-methyl-1,2-cyclopentadiene, 1-methyl-1,3-cyclopentadiene, 2-methyl-1,3-cyclopentadiene, 3-methyl-1,3-cyclopentadiene, 1,2-cycloheptadiene, 1,3-cycloheptadiene, 1,4-cycloheptadiene, 1-methyl-1,2-cyclohexadiene, 1-methyl-1,3-cyclohexadiene, 2-methyl-1,3-cyclohexadiene, 2-methyl-1,4-cyclohexadiene, 1-ethyl-1,2-cyclopentadiene, 1-ethyl-1,3-cyclopentadiene, 2-ethyl-1,3-cyclopentadiene, 1,2-dimethyl-1,2-cyclopentadiene, 1,2-dimethyl-1,3-cyclopentadiene, 1,3-dimethyl-1,3-cyclopentadiene, 1-methyl-1,3-cyclohexadiene, 1,2-dimethyl-1,3-cyclohexadiene, 1,3-dimethyl-1,3-cyclohexadiene, 1,2,3-trimethyl-1,3-cyclohexadiene, and mixtures thereof; in particular 1,3-cyclohexadiene.

Any suitable weight ratio of the solvent to the hydrocarbon containing feed mixture can be employed. Generally, the solvent to feed weight ratio is in the range of from about 1:1 to about 40:1, preferably in the range of from about 5:1 to about 20:1. When one of the above-described mixtures of two compounds (e.g., a mixture of cyclohexanol and tetraethylene glycol) is used as solvent, any weight ratio of the two solvent components can be employed, such as from about 0.01:1 to about 100:1, preferably about 1:5 to about 5:1. The solvent components are either commercially available or can be prepared by known methods. The preparation of N-methyl-2-thiopyrrolidone (also referred to as 2-methylpyrrolidone-2-thione) is described in U.S. Pat. Nos. 4,956,476, 4,990,628 and 5,003,082.

Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 100° to about 300° F., preferably in the range of from about 150° to about 250° F. Solvent and feed are generally preheated (generally to a temperature close to the column temperature of the corresponding entry point) before they are introduced into the column. Any suitable pressure can be employed during the extractive distillation. Generally the pressure is about 5 to about 100 psig, preferably about 8 to about 20 psig.

In the first embodiment of this invention, the overhead distillate product (withdrawn from the top of the column) contains a smaller volume percentage of the alkadiene(s) than the feed and a larger volume percentage of the alkene(s) than the feed, and the bottoms product (a portion of which can be reheated and recycled to the lower portion of the column) contains a larger volume percentage of the alkadiene(s) than the feed and a smaller volume percentage of the alkene(s) than the feed. In the second embodiment of this invention, the overhead distillate product contains a smaller percentage of the cycloalkadiene(s) than the feed and a larger percentage of the alkadiene(s) than the feed, and the bottoms product contains a larger volume percentage of the cycloalkadiene(s) than the feed and a smaller volume percentage of the alkadiene(s) than the feed. The bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. In the first embodiment of this invention, the feed mixture comprising alkadiene(s) and close-boiling alkene(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in alkene(s) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in alkene(s) and a bottoms stream predominantly comprising the alkadiene(s) and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising alkadiene(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., alkadiene(s) of high purity (preferably higher than 95%), through conduit 36.

A bottoms stream predominantly comprising the solvent is withdrawn from a lower portion of distillation column 29 through conduit 38. A portion of this bottom stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The above description of FIG. 1 and the various process steps can also be applied to the second embodiment of this invention which employs a feed mixture of cycloalkadiene(s) and alkadiene(s) by replacing "alkadiene(s)", wherever it occurs in the description, with "cycloalkadiene(s)", and by replacing "alkene(s)", wherever it occurs in the description, with "alkadiene(s)". Thus, in the second embodiment of the process of this invention, alkadiene(s) accumulate in the overhead stream and "cycloalkadienes" accumulate in the bottoms product.

The following examples are presented to further illustrate the invention and are not to be considered unduly limiting the scope of this invention.

EXAMPLE I

This example demonstrates the use of various solvents in the extractive distillation of an alkadiene/alkene feed.

To a hydrocarbon mixture of 50 weight-% 1,5-hexadiene and 50 weight-% 1-hexene was added an extractive solvent at various solvent:feed weight ratios. The total mixture (including the extractive solvent) was heated under reflux conditions for about 20–30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 1,5-hexadiene and 1-hexene in the liquid phase and in the vapor phase were determined by means of a gas chromatograph. The relative volatility $R^1$ was calculated as follows:

$$R^1 = \frac{Y1/Y2}{X1/X2} = \frac{Y1/X1}{Y2/X2}.$$

wherein Y1 and Y2 are the mole fractions of 1-hexene and 1,5-hexadiene, respectively, in the vapor phase; and X1 and X2 are the mole fractions of 1-hexene and 1,5-hexadiene, respectively, in the liquid phase.

The following solvents were tested: N-methyl-2-thiopyrrolidone (Thio-NMP; TNMP), N-methyl-2-pyrrolidone (NMP), a mixture of 75 weight-% TNMP and 25 weight-% cyclotetramethylene sulfone (also referred to as sulfolane); a mixture of 50 weight-% TNMP and 50 weight-% sulfolane, a mixture of 25 weight-% TNMP and 75 weight-% sulfolane, a mixture of 50 weight-% NMP and 50 weight-% sulfolane, and a mixture of 25 weight-% NMP and 75 weight-% sulfolane. Test results are summarized in Table I.

TABLE I

| Solvent:Feed Weight Ratio | Added Solvent | Relative Volatility $R^1$ |
| --- | --- | --- |
| 3:1 | TNMP | 1.2 |
| 3:1 | NMP | 1.15 |
| 3:1 | SULFOLANE | 1.05 |
| 3:1 | 75/25 TNMP/SULFOLANE | 1.16 |
| 3:1 | 50/50 TNMP/SULFOLANE | 1.18 |
| 3:1 | 25/75 TNMP/SULFOLANE | 1.08 |
| 3:1 | 50/50 NMP/SULFOLANE | 1.15 |
| 3:1 | 25/75 NMP/SULFOLANE | 1.09 |
| 5:1 | TNMP | 1.21 |
| 5:1 | NMP | 1.17 |
| 5:1 | SULFOLANE | 1.13 |
| 5:1 | 75/25 TNMP/SULFOLANE | 1.20 |
| 5:1 | 50/50 TNMP/SULFOLANE | 1.30 |
| 5:1 | 25/75 TNMP/SULFOLANE | 1.20 |
| 5:1 | 50/50 NMP/SULFOLANE | 1.23 |
| 5:1 | 25/75 NMP/SULFOLANE | 1.21 |
| 7:1 | TNMP | 1.22 |
| 7:1 | NMP | 1.17 |
| 7:1 | SULFOLANE | 1.20 |
| 7:1 | 75/25 TNMP/SULFOLANE | 1.22 |

TABLE I-continued

| Solvent:Feed Weight Ratio | Added Solvent | Relative Volatility $R^1$ |
|---|---|---|
| 7:1 | 50/50 TNMP/SULFOLANE | 1.31 |
| 7:1 | 25/75 TNMP/SULFOLANE | 1.32 |
| 7:1 | 50/50 NMP/SULFOLANE | 1.24 |
| 7:1 | 25/75 NMP/SULFOLANE | 1.31 |

Based on the test results in Table I, it is concluded that N-methyl-2-thiopyrrolidone, alone or in admixture with tetramethylene sulfone (sulfolane), will be more effective than NMP alone or sulfolane alone as solvent in the separation of $C_4$-$C_9$ alkadienes from close-boiling alkenes by extractive distillation. It is also concluded that mixtures of N-methyl-2-pyrrolidone and cyclotetramethylene sulfone (sulfolane) will be more effective than NMP alone or sulfolane alone as solvent in the separation of $C_4$-$C_9$ alkadienes from close-boiling alkenes by extractive distillation.

EXAMPLE II

This example illustrates the use of N-methyl-2-thiopyrrolidone (TNMP) as solvent in the extractive distillation of a cycloalkadiene/alkadiene feed.

Tests were carried out substantially in accordance with the procedure described in Example I, except that a mixture of 50 weight-% 1,3-cyclohexadiene and 50 weight-% 2-methyl-1,3-pentadiene was used as the hydrocarbon feed. TNMP and NMP (N-methyl-2-pyrrolidone) were used as solvents. The relative volatility $R^2$ was calculated as follows:

$$R^2 = \frac{Y3/Y4}{X3/X4} = \frac{Y3/X3}{Y4/X4}.$$

wherein Y3 and Y4 are the mole fractions of 2-methyl-1,3-pentadiene and 1,3-cyclohexadiene, respectively, in the vapor phase; and X3 and X4 are the mole fractions of 2-methyl-1,3-pentadiene and 1,3-cyclohexadiene, respectively, in the liquid phase. Test results are summarized in Table II.

TABLE II

| Solvent:Feed Weight Ratio | Added Solvent | Relative Volatility $R^2$ |
|---|---|---|
| 1:1 | TNMP | 1.26 |
| 1:1 | NMP | 1.23 |
| 3:1 | TNMP | 1.38 |
| 3:1 | NMP | 1.30 |
| 5:1 | TNMP | 1.43 |
| 5:1 | NMP | 1.32 |
| 7:1 | TNMP | 1.46 |
| 7:1 | NMP | 1.38 |

Based on the test results of Table II, it is concluded that N-methyl-2-thiopyrrolidone (TNMP) will be more effective than N-methyl-2-pyrrolidone (NMP) as solvent in the separation of $C_5$-$C_9$ cycloalkadienes from close-boiling alkadienes by extractive distillation.

Reasonable variations, modifications and adaptations for various usages and conditions can be made within the scope of the disclosure and the appended claims, without departing from the scope of this invention.

That which is claimed is:

1. A process for separating at least one alkadiene containing 4-9 carbon atoms per molecule from at least one alkene containing 4-10 carbon atoms per molecule comprising extractive distillation of a feed which consists essentially of said at least one alkadiene and said at least one alkene employing a solvent consisting essentially of N-methyl-2-thiopyrrolidone;

wherein said process produces (i) an overhead product which contains a smaller volume percentage of said at least one alkadiene and a larger volume percentage of said one alkene than said feed, and (ii) a bottoms product which contains said solvent and a larger volume percentage of said at least one alkadiene and a smaller volume percentage of said at least one alkene than said feed; and wherein said at least one alkadiene is separated from said solvent contained in said bottoms product.

2. A process in accordance with claim 1, wherein said at least one alkadiene is 1,5-hexadiene and said at least one alkene is selected from the group consisting of 1-hexane and 2-heptene.

3. A process in accordance with claim 1, wherein said feed boils at a temperature in the range of about 15° F. to about 400° F., at atmospheric pressure conditions.

4. A process in accordance with claim 1, wherein the weight ratio of said solvent to said feed is in the range of about 1:1 to about 40:1.

5. A process for separating at least one cycloalkadiene containing 5-9 carbon atoms per molecule from at least one alkadiene containing 4-9 carbon atoms per molecule comprising extractive distillation of a feed which consists essentially of said at least one cycloalkadiene and said at least one alkadiene employing a solvent consisting essentially of N-methyl-2-thiopyrrolidone;

wherein said process produces (i) an overhead product which contains a smaller volume percentage of said one cycloalkadiene and a larger volume percentage of said at least one alkadiene than said feed, and (ii) a bottoms product which contains said solvent and a larger volume percentage of said at least one cycloalkadiene and a smaller volume percentage of said at least one alkadiene than said feed; and wherein said at least one cycloalkadiene is separated from said solvent contained in said bottoms product.

6. A process in accordance with claim 5, wherein said at least one cycloalkadiene is 1,3-cyclohexadiene and said at least one alkadiene is 2-methyl-1,3-pentadiene.

7. A process in accordance with claim 5, wherein said feed boils at a temperature in the range of about 80° F. to about 400° F., atmospheric pressure conditions.

8. A process in accordance with claim 5, wherein the weight ratio of said solvent to said feed is in the range of about 1:1 to about 40:1.

9. A process for separating at least one alkadiene containing 4-9 carbon atoms per molecule from at least one alkene containing 4-10 carbon atoms per molecule comprising extractive distillation of a feed which consists essentially of said at least one alkadiene and said at least one alkene employing a solvent consisting essentially of a mixture of cyclotetramethylene sulfone and N-methyl-2-thiopyrrolidone;

wherein said process produces (i) an overhead product which contains a smaller volume percentage of said at least one alkadiene and a larger volume percentage of said at least one alkene than said feed, and (ii) a bottoms product which contains said solvent and a larger volume percentage of said at least one alkadiene and a smaller volume percentage of said at least one alkene than said feed; and wherein said at least one alkadiene is separated from said solvent contained in said bottoms product.

10. A process in accordance with claim 9, wherein said at least one alkadiene is 1,5-hexadiene and said at least one alkene is selected from the group consisting of 1-hexene and 2-heptene.

11. A process in accordance with claim 9, wherein said feed boils at a temperature in the range of about 15° to about 400° F., at atmospheric pressure conditions.

12. A process in accordance with claim 9, wherein the weight ratio of cyclotetramethylene sulfone to N-methyl-2-thiopyrrolidone in said solvent is in the range of about 0.01:1 to about 100:1.

13. A process in accordance with claim 9, wherein the weight ratio of said solvent to said feed is in the range of about 1:1 to about 40:1.

* * * * *